United States Patent [19]

Arrang et al.

[11] Patent Number: 4,707,487
[45] Date of Patent: Nov. 17, 1987

[54] (4-IMIDAZOLYL)PIPERIDINES, THE PREPARATION THEREOF AND THEIR APPLICATION IN THERAPY

[75] Inventors: Jean-Michel Arrang, Gif /Yvette; Monique Garbarg, Paris; Jean-Charles Lancelot, Tour En Bessin; Jeanne-Marie Lecomte, Paris; Max-Fernand Robba, Caen; Jean-Charles Schwartz, Paris, all of France

[73] Assignees: Institut National de la Sante et de la Recherche Medicale (Inserm), Paris; Universite de Caen, Caen; Societe Civile Bioprojet, Paris, all of France

[21] Appl. No.: 840,956

[22] Filed: Mar. 17, 1986

[30] Foreign Application Priority Data

Mar. 26, 1985 [FR] France .............................. 85 04496

[51] Int. Cl.[4] .................. C07D 401/04; C07D 405/14; A61K 31/445
[52] U.S. Cl. ........................... 514/326; 514/321; 514/322; 546/197; 546/199; 546/210
[58] Field of Search ...................... 546/197, 199, 210; 514/321, 322, 326

[56] References Cited

U.S. PATENT DOCUMENTS 4,087,531  5/1978  Langbein et al. .................. 546/210
4,217,350  8/1980  Eichenberger et al. ............ 546/210
4,329,348  5/1982  Huebner ............................ 546/210

OTHER PUBLICATIONS

"Structure-Action Relationship of Histamine Analogs 1. Histamine-Like Compounds With Cyclized Side Chain", *Chemical Abstracts*, vol. 80, No. 15, Apr. 15, 1974, No. 82801a, p. 389.

*Primary Examiner*—Robert T. Bond
*Attorney, Agent, or Firm*—Young & Thompson

[57] ABSTRACT

Compounds of general formula

I in which $R_1$ denotes H, $CH_3$ or $C_2H_5$, R denotes H or $R_2$ and $R_2$ denotes an alkyl, piperonyl, 3-(1-benzimidazolonyl)-propyl group; a group of formula $$-(CH_2)_n-X-\bigcirc-R_3$$

in which n is 0, 1, 2, or 3, X is a single bond or alternatively —O—, —S—, —NH—, —CO—, —CH=CH— or $$-CH-\bigcirc-R_3,$$

and $R_3$ is H, $CH_3$, F, CN or an acyl group; or alternatively a group of formula $$-\underset{\underset{Z}{\parallel}}{C}-NH-R_5$$

in which Z denotes an O or S atom or a divalent group NH, N —$CH_3$ or N —CN, and $R_5$ denotes an alkyl group, a cycloalkyl group which can bear a phenyl substituent, a phenyl group which can bear a $CH_3$ or F substituent, a phenylalkyl(1-3 C) group or a naphthyl, adamantyl or p-toluenesulphonyl group. These compounds are useful to control the release of cerebral histamine and to increase the rate of renewal of cerebral histamine.

12 Claims, No Drawings

(4-IMIDAZOLYL)PIPERIDINES, THE PREPARATION THEREOF AND THEIR APPLICATION IN THERAPY

The present invention relates to (4-imidazolyl)-piperidines, the preparation thereof and their application in therapy, linked to a new mechanism of action.

The compounds of the invention correspond to the general formula

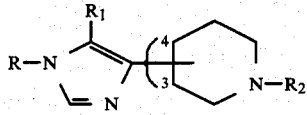

in which
$R_1$ denotes a hydrogen atom or a methyl or ethyl group,
R denotes a hydrogen atom or a radical $R_2$, and
$R_2$ denotes a linear or branched alkyl group having 1 to 6 carbon atoms; a piperonyl group, a 3-(1-benzimidazolonyl)propyl group; a group of formula

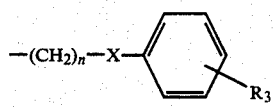

in which n is 0, 1, 2 or 3, X is a single bond or alternatively —O—, —S—, —NH—, —CO—, —CH═CH— or

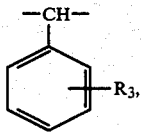

and $R_3$ is H, $CH_3$, halogen, CN, $CF_3$ or an acyl group —$COR_4$, $R_4$ being a linear or branched alkyl group having 1 to 6 carbon atoms, a cycloalkyl group having 3 to 6 carbon atoms or a phenyl group which can bear a $CH_3$ or F substituent; or alternatively a group of formula

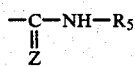

in which Z denotes an O or S atom or a divalent group NH, N—$CH_3$ or N—CN and $R_5$ denotes a linear or branched alkyl group having 1 to 8 carbon atoms, a cycloalkyl group having 3 to 6 carbon atoms which can bear a phenyl substituent, a cycloalkyl(3 to 6 C)alkyl(1 to 3 C, linear or branched) group, a phenyl group which can bear a $CH_3$, halogen or $CF_3$ substituent, a phenylalkyl(1 to 3 C, linear or branched) group or a naphthyl, adamantyl or p-toluenesulphonyl group, as well as the pharmaceutically acceptable salts thereof.

A group of preferred compounds according to the invention consists of the compounds of general formula I in which $R_2$ is a group of formula

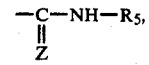

the symbols Z and $R_5$ having the meanings given above, and especially the compounds in which Z is an O or S atom or an NH group.

The compounds of the invention can be prepared by reaction of (4-imidazolyl)piperidines or one of their alkylated derivatives of the formula

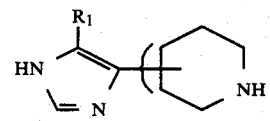

in which $R_1$ has the same meaning as in the formula I, either with a halogenated derivative $R'_2X'$, $R'_2$ having the same meaning as $R_2$ except for the group of formula

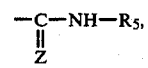

and X' denoting a halogen, or, in this latter case, with a derivative of formula Z=C=N—$R_5$ in which Z and $R_5$ have the same meaning as in the formula I and, where appropriate, partial thermal decomposition of the disubstituted derivative (I; R=$R_2$) thereby prepared, to obtain the corresponding monosubstituted derivative (I; R=H).

The compounds of formula II are known, and can be prepared according to the method of Pyman [J. Chem. Soc. (1911) 99, p.668].

The reaction with the halogenated derivative $R'_2X'$ can be performed in a known manner, for example by heating to temperatures ranging from 60° to 180° C. in a polar solvent such as dimethyl formamide and in the presence of an acceptor for acid such as an alkali metal carbonate or alkali earth metal carbonate.

The condensation reaction with the derivative of formula Z=C=N—$R_5$ (in particular, isocyanate and isothiocyanate when Z is O and S, respectively) can be performed in a known manner, for example at temperatures ranging from 80° to 130° C. under reflux in a neutral solvent such as toluene.

The thermal decomposition of the disubstituted compounds (I; R=$R_2$) can be performed by heating and sublimation at temperatures in general greater than 200° C. (for example 200° to 240° C.) and under reduced pressure.

The examples which follow illustrate the invention.

EXAMPLE 1

4-(1-CYCLOHEXYLAMINOTHIOCARBONYL-4-PIPERIDYL)-1H-IMIDAZOLE 1.4 g (0.0092 mole) of 4-(4-piperidyl)-1H-imidazole and 1.42 g (0.010 mole) of cyclohexyl isothiocyanate are brought to reflux for 2 hours in 100 $cm^3$ of anhydrous toluene. Precipitate formed on cooling is drained, washed with anhydrous ethyl ether, dried and recrystallized in toluene. White powder, M.p. (d.) 170° C., w=2 g. 74% yield. IR spectrum (KBr): 3240 (NH). Principal bands: 2920, 2840, 1520, 1440, 1350, 1330, 1250, 1175, 1090, 970, 830, 755 and 695 $cm^{-1}$.

NMR spectrum: DMSO-d$_6$δH, imidazole: 7.45 and 6.66.

coupling constant J$_{H2-H5}$=0.90 Hz.

δNH: 7.13 and 7.05 ppm.

δH piperidine and cyclohexyl: 4.61, 4.16, 2.98, 1.76 and 1.20 ppm.

Examples 6, 7, 31, 45, 46, 57, and 59 to 62 in TABLE 1 are prepared in a similar manner.

EXAMPLE 2

4-(1-CYCLOHEXYLAMINOCARBONYL-4-PIPERIDYL)-1-CYCLOHEXYLAMINOCARBONYL-1H-IMIDAZOLE 1 g (0.0066 mole) of 4-(4-piperidyl)-1H-imidazole and 1.73 g (0.013 mole) of cyclohexyl isocyanate are brought to reflux for 1 hour in 80 cm$^3$ of anhydrous toluene. After the solution is cooled, the crystals formed are drained, washed with anhydrous ethyl ether, dried and recrystallized in acetonitrile. M.p. 192° C., w=1.8 g.

Yield: 67.9%.

IR spectrum (KBr) 3390 and 3210 (NH), 1695 and 1610 (C=O).

Principal bands: 3005, 2930, 2850, 1525, 1445, 1305, 1255, 1150, 1025, 970, 835 and 750 cm$^{-1}$.

NMR spectrum: DMSO-d$_6$, δH, imidazole: 8.08 and 7.36 ppm.

δNH: (doublets): 7.98 and 6.03 ppm.

δH cyclohexyl and piperidine: 4.00, 3.46, 2.68, 1.83 and 1.30 ppm.

Examples 12, 13, 14, 15, 16, 17, 18, 19, 20 and 21 in TABLE 1 are synthesized in a similar manner.

EXAMPLE 3

4-(1-CYCLOHEXYLAMINOCARBONYL-4-PIPERIDYL)-1H-IMIDAZOLE 0.6 g (0.0014 mole) of 4-(1-cyclohexylaminocarbonyl-4-piperidyl)-1-cyclohexylaminocarbonyl-1H-imidazole, obtained according to Example 2, are heated to 220° C. for 5 minutes and then sublimed under 0.05 mmHg (6.5 Pa). White crystals, M.p. 166° C., w=0.24 g. Yield: 63%. IR spectrum (KBr): 3200 (NH), 1610 (C=O). Principal bands at 2920, 2850, 1530, 1440, 1365, 1235, 1140, 1015, 975, 825, 765 and 630 cm$^{-1}$.

NMR spectrum: DMSO-d$_6$: δH imidazole: 7.36 and 6.60 ppm.

δNH: 5.91 and 6.00 ppm.

δH cyclohexyl and piperidine: 3.90, 3.83, 2.56, 1.66 and 1.10 ppm.

Examples 8 to 11 and 58 (TABLE 1) are prepared in a similar manner.

EXAMPLE 4

4-[1-(4-CYCLOPROPYLCARBONYLPHENYL)-4-PIPERIDYL]-1H-IMIDAZOLE 3 g (0.019 mole) of 4-(4-piperidyl)-1H-imidazole and 3.39 g (0.016 mole) of γ-chloro-p-fluorobutyrophenone are stirred in 70 cm$^3$ of dimethylformamide for 5 minutes, 4 g (0.037 mole) of sodium carbonate and 0.2 g (0.0012 mole) of potassium iodide are then added and the solution is brought to 160° C. for 3 hours. After being cooled, the solution is poured into 200 cm$^3$ of water and stirred for 1 hour. The precipitate formed is drained, washed with water, dried and recrystallized in acetonitrile.

Yellowish powder, M.p. 198° C., w=0.6 g.

Yield: 11%.

IR spectrum (KBr): 3070 (NH), 1640 (C=O), principal bands at 2920, 2820, 1595, 1385, 1230, 1100, 1035, 990, 830 and 765 cm$^{-1}$.

NMR spectrum: DMSO-d$_6$δphenyl: 7.86 and 6.95 ppm.

δimidazole: 7.45 and 6.70 ppm.

δ(NH): 4.46 ppm; piperidine: complex, 3.96, 3.33, 2.8 and 1.8 ppm.

δcyclopropyl: 0.93 ppm.

EXAMPLE 5

4-[1-(4-PROPIONYLPHENYL)-4-PIPERIDYL]-1H-IMIDAZOLE 3 g (0.019 mole) of 4-(4-piperidyl)-1H-imidazole and 2.88 g (0.019 mole) of para-fluoropropiophenone are stirred in 70 cm$^3$ of dimethylformamide for 5 minutes. 4 g (0.037 mole) of disodium carbonate and 0.2 g (0.0012 mole) of potassium iodide are added and the solution is brought to 160° C. for 3 hours. After being cooled, the solution is poured into 200 cm$^3$ of water and stirred for 1 hour. The precipitate formed is drained, washed with water, dried and recrystallized in acetonitrile.

Yellow powder, M.p. 210° C. Yield: 13%.

Examples 22, 23, 24, 25 and 26 in TABLE 1 are prepared in a similar manner.

EXAMPLE 27

1-(p-FLUOROBENZYL)-4-(4-IMIDAZOLYL)-PIPERIDINE

To a solution of 1.5 g of 4-(4-imidazolyl)piperidine in 75 cm$^3$ of dimethyl formamide, 2 g of potassium carbonate and 1.5 g of p-fluorobenzyl chloride are added. The mixture is then heated to 80° C. with stirring for 2 hours. The mixture is filtered and the filtrate evaporated under reduced pressure. The residue is recrystallized in acetonitrile. White crystals, M.p. 232° C.

Yield: 70%, C$_{15}$H$_{18}$FN$_3$ (M=259.02).

Examples 28 to 30, 32 to 44 and 47 to 56 in TABLE 1 are prepared in a similar manner.

The compounds of the preceding examples, and also other compounds of formula I given by way of examples, are collated in Table 1 below.

The piperidine is in position 4 with respect to the imidazole in Examples 1 to 58, and in position 3 in the other examples (*).

The compounds were purified either using the solvent indicated, or as follows:

(a) Purification by sublimation at 240° C. under 0.05 mm (6.5 Pa).

(b) Purification by sublimation at 210° C.–220° C. under 0.05 mm.

(c) Purification by sublimation at 200° C. under 0.05 mm.

(d) Purification by sublimation at 200° C. under 0.05 mm.

TABLE 1
| Ex. No | R | R₁ | R₂ | Melting Point (°C.) | Yld. (%) | Crystallization solvent |
|---|---|---|---|---|---|---|
| 1 | H | H | 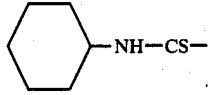 | 170 (d.) | 74 | toluene |
| 2 | 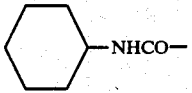 | H | 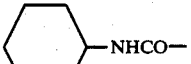 | 192 | 67,9 | acetonitrile |
| 3 | H | H | 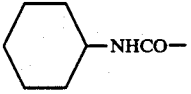 | 166 | 63 | (b) |
| 4 | H | H | 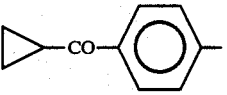 | 198 | 11 | acetonitrile |
| 5 | H | H | 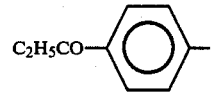 | 210 | 13 | acetonitrile |
| 6 | H | H | 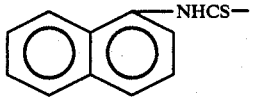 | 164 | 70 | acetonitrile |
| 7 | H | H | 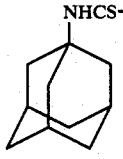 | 142 | 32 | toluene |
| 8 | H | H | 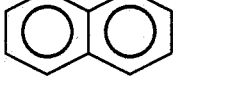 | 150 | 34 | (a) |
| 9 | H | H | 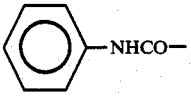 | 120 | 47 | (b) |
| 10 | H | H | 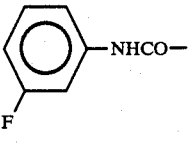 | 138 | 43 | (c) |
| 11 | H | H | 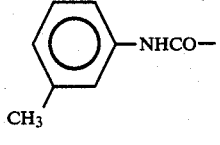 | 118 | 26 | (d) |
| 12 | CH₃NHCO— | H | CH₃NHCO— | 178 | 57 | toluene |
| 13 | 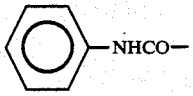 | H | 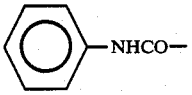 | 178 | 58 | toluene |

TABLE 1-continued

| Ex. No | R | $R_1$ | $R_2$ | Melting Point (°C.) | Yld. (%) | Crystallization solvent |
|---|---|---|---|---|---|---|
| 14 | 3-F-C$_6$H$_4$-NHCO- | H | 3-F-C$_6$H$_4$-NHCO- | 176 | 44 | toluene |
| 15 | 4-F-C$_6$H$_4$-NHCO- | H | 4-F-C$_6$H$_4$-NHCO- | 220 | 32 | toluene |
| 16 | 3-CH$_3$-C$_6$H$_4$-NHCO- | H | 3-CH$_3$-C$_6$H$_4$-NHCO- | 154 | 68 | acetonitrile |
| 17 | 4-CH$_3$-C$_6$H$_4$-SO$_2$NHCO- | H | 4-CH$_3$-C$_6$H$_4$-SO$_2$NHCO- | 260 | 52 | toluene |
| 18 | 2-naphthyl-NHCO- | H | 2-naphthyl-NHCO- | 154 | 64 | toluene |
| 19 | C$_6$H$_5$-CH$_2$NHCO- | H | C$_6$H$_5$-CH$_2$NHCO- | 156 | 72 | toluene |
| 20 | C$_6$H$_5$-CH(CH$_3$)-NHCO- | H | C$_6$H$_5$-CH(CH$_3$)-NHCO- | 142 | 83 | toluene |
| 21 | C$_6$H$_5$-cyclopropyl-NHCO- | H | C$_6$H$_5$-cyclopropyl-NHCO- | 220 | 60 | toluene |
| 22 | 4-NC-C$_6$H$_4$- | H | 4-NC-C$_6$H$_4$- | 214 | 12 | toluene |
| 23 | 4-CH$_3$CO-C$_6$H$_4$- | H | 4-CH$_3$CO-C$_6$H$_4$- | 182 | 17 | acetone |
| 24 | 4-C$_2$H$_5$CO-C$_6$H$_4$- | H | 4-C$_2$H$_5$CO-C$_6$H$_4$- | 218 | 24 | acetonitrile |
| 25 | 4-(cyclopropyl-CO)-C$_6$H$_4$- | H | 4-(cyclopropyl-CO)-C$_6$H$_4$- | 218 | 15 | acetonitrile |

TABLE 1-continued

| Ex. No | R | R₁ | R₂ | Melting Point (°C.) | Yld. (%) | Crystallization solvent |
|---|---|---|---|---|---|---|
| 26 | C₆H₅CO—⟨phenyl⟩— | H | C₆H₅CO—⟨phenyl⟩— | 172 | 24 | acetone |
| 27 | H | H | F—⟨phenyl⟩—CH₂— | 232 | 70 | acetonitrile |
| 28 | H | H | —CH₃ | 82 | 60 | ethyl ether |
| 29 | H | H | —CH(CH₃)₂ | 158 | 65 | ethyl acetate |
| 30 | H | CH₃ | —CH(CH₃)₂ | 192 | 70 | acetonitrile |
| 31 | H | H | —C(=NCN)NCH₃ | 134 | 40 | ethyl acetate |
| 32 | H | H | —CH₂—⟨phenyl⟩ | 105 | 70 | ethyl ether |
| 33 | H | H | —CH₂CH₂—⟨phenyl⟩ | 103 | 75 | ethyl ether |
| 34 | H | H | —CH₂CH₂NH—⟨phenyl⟩ | 84 | 60 | ethyl ether |
| 35 | H | H | —CH₂CH=CH—⟨phenyl⟩ | 138 | 75 | ethyl acetate |
| 36 | H | CH₃ | —CH₂—⟨benzodioxane⟩ | 196 | 45 | acetonitrile |
| 37 | H | CH₃ | —CH₂CH₂—⟨phenyl⟩—F | 182 | 40 | acetonitrile |
| 38 | H | H | —(CH₂)₃CO—⟨phenyl⟩—F | 198 | 45 | ethyl ether |

TABLE 1-continued

| Ex. No | R | R₁ | R₂ | Melting Point (°C.) | Yld. (%) | Crystallization solvent |
|---|---|---|---|---|---|---|
| 39 | H | CH₃ | —CH₂—CH₂—CH₂—(benzimidazol-2(3H)-one-N-yl) | 176 | 55 | acetonitrile |
| 40 | H | H | —CH₂CH₂O—C₆H₅ | 92 | 60 | ethyl ether |
| 41 | H | H | —(CH₂)₃O—C₆H₄—F | 112 | 75 | ethyl acetate |
| 42 | H | H | —CH₂CH₂CH(C₆H₅)₂ | 96 | 70 | ethyl ether |
| 43 | H | H | —(CH₂)₃CH(C₆H₄F—p)₂ | 104 | 60 | ethyl ether |
| 44 | H | CH₃ | CH₃ | 186 | 70 | ethyl ether |
| 45 | H | H | —C(=S)NHCH₃ | 206 | 50 | ethyl acetate |
| 46 | H | CH₃ | —C(=S)NHCH₃ | 212 | 55 | ethyl acetate |
| 47 | H | CH₃ | —CH₂—C₆H₅ | 205 | 70 | ethyl ether |
| 48 | H | CH₃ | —CH₂—C₆H₄—F | 229 | 75 | ethyl ether |
| 49 | H | CH₃ | —CH(C₆H₅)₂ | 158 | 60 | acetone |
| 50 | H | CH₃ | —(CH₂)₂CH(C₆H₅)₂ | 195 | 70 | ethyl ether |
| 51 | H | H | —(CH₂)₂—C₆H₄—F | 152 | 60 | acetonitrile |
| 52 | H | CH₃ | —(CH₂)₃O—C₆H₄—F | 144 | 70 | ethyl acetate |
| 53 | H | CH₃ | —(CH₂)₃CO—C₆H₄—F | 132 | 70 | ethyl ether |
| 54 | H | CH₃ | —(CH₂)₃CH(C₆H₄p-F)₂ | 132 | 75 | ethyl ether |
| 55 | H | H | —CH₂—CH(1,4-benzodioxane) | 148 | 50 | acetonitrile |

TABLE 1-continued

| Ex. No | R | R₁ | R₂ | Melting Point (°C.) | Yld. (%) | Crystallization solvent |
|---|---|---|---|---|---|---|
| 56 | H | H | Ph−CH(CH₃)−NHCO− | 131 | 63 | toluene |
| 57 | H | H | cyclopropyl−CH(CH₃)−NH−C(=NH)− | 162 | 59 | toluene |
| 58* | H | H | cyclohexyl−NH−CS− | 214 | 92 | acetonitrile |
| 59* | H | H | 1-adamantyl−NHCS− | 140 (d.) | 65 | acetonitrile |
| 60* | H | H | naphthyl−NHCS− | 212 | 77 | acetonitrile |
| 61* | H | H | Ph−NHCO− | 135 | 40 | acetonitrile |
| 62 | H | H | 2-CH₃-C₆H₄−NHCS− | 170 | 40 | acetonitrile |
| 63 | H | H | 2-OCH₃-C₆H₄−NHCS− | 154 | 50 | toluene |
| 64 | H | H | 4-CH₃O-C₆H₄−NHCS− | 172 | 71 | acetonitrile |
| 65 | H | H | 4-F-C₆H₄−NHCS− | 162 | 61 | acetonitrile |
| 66 | H | H | Ph−NHCS− | 134 | 80 | toluene |
| 67 | H | H | 2-Cl-C₆H₄−NHCS− | 108 | 52 | toluene |

TABLE 1-continued

| Ex. No | R | R₁ | R₂ | Melting Point (°C.) | Yld. (%) | Crystallization solvent | |
|---|---|---|---|---|---|---|---|
| 68 | H | H | 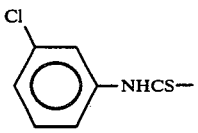 | 124 | 41 | toluene | |
| 69 | H | H | 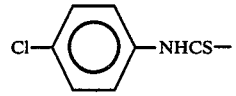 | 138 | 64 | toluene | |
| 70 | H | H | 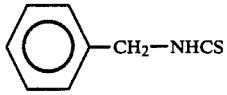 | 178 | 72 | acetonitrile | |
| 71 | 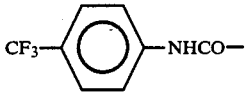 | H | 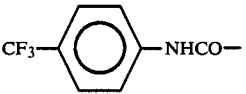 | 192 | 76 | acetonitrile | |
| 72 | H | H | 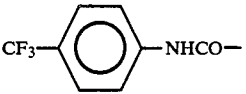 | 107 | 35 | sublimation 200°/0,05 mm | |
| 73 | H | H | 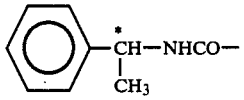 | 76 | 35 | Sublimation 200°/0,05 mm | (a) |
| 74 | H | H | 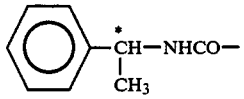 | 86 | 40 | Sublimation 210°/0,05 mm | (b) |
| 75 | H | H | 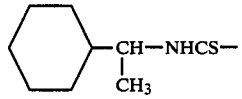 | 181 | 49 | toluene | [R.S] |
| 76 | H | H | 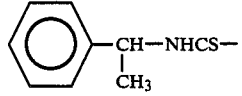 | 139 | 41 | toluene | [R.S] |
| 77 | H | H | 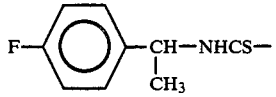 | 131 | 37 | acetonitrile | [R.S] |
| 78 | H | H | 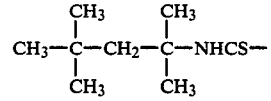 | 142 | 65 | acetonitrile | |

(a) dextrorotatory isomer $\alpha_D = +35°\ 33$
(b) levorotatory isomer $\alpha_D = -36°\ 66$

PHARMACOLOGICAL STUDY

A pharmacological study of the compounds of the invention has for the first time enabled blocking of the H₃ histaminergic receptors controlling the release of cerebral histamine to be demonstrated in vitro, and an increase in the rate of renewal of cerebral histamine to be demonstrated in vivo, which effects establish, in particular, a psychotropic action.

The pharmacological tests carried out were as follows:

I. ACUTE TOXICITY

The determination of mortality in mice is observed folowing a single intravenous administration of increasing doses of compounds to be tested.

The L.D.$_{50}$ for all the compounds studied is greater than 100 mg/kg (i.p.). For example, that for the derivative No. 1 is 100 mg/kg after one hour.

II. ANTAGONISM OF HISTAMINE STIMULATION OF THE H$_3$ RECEPTORS CONTROLLING THE RELEASE OF ($^3$H)HISTAMINE INDUCED BY DEPOLARIZATION OF SECTIONS OF RAT BRAIN

The method described by Arrang et al., (Nature 1983, 302: 838–837) is used on sections (0.3 mm thick) of cerebral cortex of male Wistar rats (180–200 g) (IFFA-CREDO, France).

Exogenous histamine (at a concentration of 1 $\mu$M) produces an approximately 60% inhibition of release. This effect is gradually reversed in the presence of H$_3$ antagonists, added in increasing concentrations. The concentration of these antagonists for which the effect of exogenous histamine is reduced by one half (IC$_{50}$) is determined, and the apparent inhibition constant (Ki) is then calculated according to Cheng and Prussof (Biochem. Pharmacol. 1973, 22, 3099–3108), taking into account the 50% effective concentration of histamine (EC$_{50}$=0.13 $\mu$M). The results are collated in Table 2 below. Moreover, it has been verified on some compounds that the inhibition can be fully overcome by increasing the concentration of exogenous histamine.

TABLE 2
APPARENT DISSOCIATION CONSTANTS (Ki) OF VARIOUS DERIVATIVES AS ANTAGONISTS OF HISTAMINE ON THE H$_3$ SELF-RECEPTORS OF RAT BRAIN

| EXAMPLE No. | (Ki) (nM) |
| --- | --- |
| 1 | 5 |
| 2 | 26 |
| 3 | 41 |
| 4 | 37 |
| 7 | 30 |
| 9 | 170 |
| 10 | 23 |
| 11 | 52 |
| 16 | 84 |
| 20 | 22 |
| 39 | 500 |
| 40 | 67 |
| 56 | 10 |
| 57 | 12 |
| 58 | 40 |

III. EFFECTS OF H$_3$ ANTAGONISTS ON THE RATE OF RENEWAL OF CEREBRAL HISTAMINE

The rate of renewal of histamine in the cerebral cortex of the rat was estimated by studying the decrease in the histamine level after blocking of its synthesis with $\alpha$-fluoromethylhistidine ($\alpha$-FMH), an irreversible inhibitor of its synthesizing enzyme, histidine decarboxylase.

Male rats weighing from 80 to 100 g simultaneously receive intraperitoneally $\alpha$-fluoromethyl histidine and the compound to be tested, each at a dose of 20 mg/kg. One hour later, the animals are sacrificed and the cerebral cortex rapidly removed and homogenized in 10 volumes of 0.32 M sucrose. The homogenate thereby obtained is subjected to two successive centrifugations, the first at $10^4$ g.min and second at $2\times10^5$ g.min to sediment the fraction enriched in synaptosomes (Whittaker, Michaelson and Kirkland, Biochem. J., 1967, 90, 293–305). After resuspension of this fraction in 10 volumes of 20 mM phosphate (K$_2$/K) buffer, PH 7.8, and treatment with ultrasound, an aliquot portion is frozen for subsequent assay of histidine decarboxylase activity (Baudry, Martres and Schwartz, J. Neurochem., 21, 1301–1309, 1973), and another portion is heated for 10 minutes at 95° C. and then centrifuged at $10^4$ g.min. The endogenous histamine is determined in the supernatant by a radioenzymatic assay, which enables the histamine to be converted to tritiated N$^w$ methylhistamine by means of an enzyme purified from rat kidney, histamine N-methyltransferase, and a tritiated methyl radical donor, S-adenosylmethionine. The N$^w$-methylhistamine thereby formed is selectively extracted in an alkaline medium into chloroform, before measurement of the tritiated product by liquid scintillation (Taylor and Snyder, J. Pharmacol. Exp. Ther., 137, 619–633, 1971). The rate of renewal of histamine is calculated from the difference between its levels before and after administration of $\alpha$-fluoromethylhistidine.

In the controls, these rates correspond to 15 ng/g/h, compared with approximately 30 ng/g/h after treatment with an H$_3$-receptor antagonist (Table 3).

In addition, the derivative of Example No. 1, administered alone at a dose of 20 mg/kg, induces a significant fall in the histamine level in the synaptosomal fraction.

TABLE 3
EFFECTS OF EXAMPLES Nos. 1 AND 3 ON THE RATE OF RENEWAL OF HISTAMINE IN THE SYNAPTOSOMAL FRACTION (P$_2$) OF RAT CEREBRAL CORTEX

| TREATMENT | HISTAMINE | DEPLETION BY $\alpha$-FMH |
| --- | --- | --- |
| Vehicle | 51.6 ± 3.0 | 0 |
| $\alpha$-FMH (20 mg/kg) | 37.1 ± 2.7 | 14.5 ± 4.0 |
| Example No. 1 (20 mg/kg) | 39.3 ± 2.1** | 12.3 ± 3.7 |
| $\alpha$-FMH (20 mg/kg) + Derivative No. 1 (2 mg/kg) | 23.2 ± 2.7* | 28.4 ± 4.0 (+96%) |
| + Derivative No. 1 (10 mg/kg) | 21.9 ± 1.0* | 29.7 ± 3.2*** (+105%) |
| + Derivative No. 1 (20 mg/kg) | 26.4 ± 1.4* | 25.2 ± 3.3 (+74%) |
| $\alpha$-FMH (20 mg/kg) + Example No. 3 (20 mg/kg) | 24.9 ± 1.2* | 26.7 ± 3.2*** (+84%) |

*$p < 0.01$ with respect to the animals treated with $\alpha$-FMH alone
**$p < 0.03$ with the untreated animals
***$p < 0.05$ with respect to the animals treated with $\alpha$-FMH.
Each group comprises 7–20 rats.

The results of these studies demonstrate the low toxicity, the advantageous antagonistic properties for the H$_3$ histamine receptors and the capacity for increasing the rate of renewal of cerebral histamine shown by the derivatives of the invention, which properties make them the first compounds of this type which are useful in human and veterinary medicine. Their therapeutic applications relate, in particular, to the central nervous system and the peripheral organs the functions of which are regulated by the H$_3$ histamine receptors.

The drug of the invention can be administered to man orally, perlingually, nasally, rectally and parenterally, the active principle being combined with a therapeutically suitable excipient or vehicle.

Each unit dose advantageously contains from 0.5 to 100 mg of active principle, and the daily administrable doses can vary from 0.5 to 200 mg of active principle.

What is claimed is:

1. A compounds corresponding to the formula

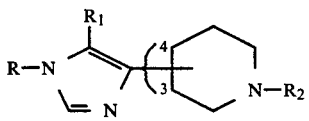     I in which
R₁ denotes a hydrogen atom or a methyl or ethyl group,
R denotes a hydrogen atom or the radical R₂, and
R₂ denotes a linear or branched alkyl group having 1 to 6 carbon atoms; a piperonyl group; a 3-(1-benzimidazolonyl)propyl group; a group of formula

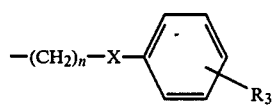

in which n is 0, 1, 2 or 3, X is a single bond or alternatively —O—, —S—, —NH—, —CO—, —CH=CH— or

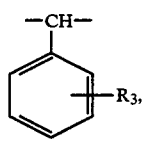

and R₃ is H, CH₃, halogen, CN, CF₃ or an acyl group —COR₄, R₄ being a linear or branched alkyl group having 1 to 6 carbon atoms, a cycloalkyl group having 3 to 6 carbon atoms or a phenyl group which can bear a CH₃ or F substituent; or alternatively a group of formula

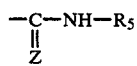

in which Z denotes an O or S atom or a divalent group NH, N—CH₃ or N—CN and R₅ denotes a linear or branched alkyl group having 1 to 8 carbon atoms, a cycloalkyl group having 3 to 6 carbon atoms which can bear a phenyl substituent, a cycloalkyl(3 to 6 C)alkyl(1 to 3 C, linear or branched) group, a phenyl group which can bear a CH₃, halogen or CF₃ substituent, a phenylalkyl(1 to 3 C, linear or branched) group or a naphthyl, adamantyl or p-toluenesulphonyl group, as well as the pharmaceutically acceptable salts thereof.

2. A compounds according to claim 1, in which R₂ denotes a group of formula

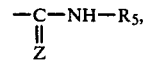

having the same meaning as in the formula I.

3. A compounds according to claim 2, in which Z is O or S or an NH group.

4. 4-(1-cyclohexylaminothiocarbonyl-4-piperidyl)-1H-imidazole.

5. 4-(1-cyclohexylaminocarbonyl-4-piperidyl)-1-cyclohexylaminocarbonyl-1H-imidazole.

6. 4-(1-cyclohexylaminocarbonyl-4-piperidyl)-1H-imidazole.

7. 4-[1-(4-cyclopropylcarbonylphenyl)-4-piperidyl]--H-imidazole.

8. 4-[1-(1-adamantylaminothiocarbonyl)-4-piperidyl]-1H-imidazole.

9. 4-[1-(m-fluorophenylaminocarbonyl)-4-piperidyl]-1H-imidazole.

10. 4-[1-(α-methylbenzylaminocarbonyl)-4-piperidyl]-1-(α-methylbenzylaminocarbonyl)-1H-imidazole.

11. Process for preparing a compounds according to claim 1, characterized in that 4-(4-imidazolyl)piperidine or one of its alkylated derivatives of formula

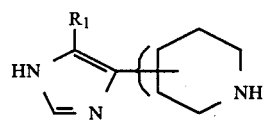     II in which R₁ has the same meaning as in the formula I, is reacted
either with a halogenated derivative R′₂X′, R′₂ having the same meaning as R₂ except for the group of formula

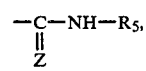

and
X′ denoting a halogen,
or, in this latter case, with a derivative of formula Z=C=N—R₅ in which Z and R₅ have the same meaning as in the formula I, and, where appropriate, partial decomposition is performed of the disubstituted derivative (I; R=R₂) thereby prepared, so as to obtain the corresponding monosubstituted derivative (I; R=H).

12. Pharmaceutical composition containing an amount effective to control the release of cerebral histimine and to increase the the rate of removal of cerebral histamine, a compound according to claim 1 and a therapeutically compatible excipient or vehicle.

* * * * *